(12) United States Patent
Folmar, Sr.

(10) Patent No.: US 11,969,321 B2
(45) Date of Patent: Apr. 30, 2024

(54) ABSORPTIVE ANAL HYGIENE APPARATUS

(71) Applicant: Ian Folmar, Sr., Columbus, OH (US)

(72) Inventor: Ian Folmar, Sr., Columbus, OH (US)

(*) Notice: Subject to any disclaimer, the term of this patent is extended or adjusted under 35 U.S.C. 154(b) by 472 days.

(21) Appl. No.: 17/143,465

(22) Filed: Jan. 7, 2021

(65) Prior Publication Data
US 2022/0211550 A1 Jul. 7, 2022

(51) Int. Cl.
*A61F 13/15* (2006.01)
*A61F 13/20* (2006.01)
*A61F 13/34* (2006.01)

(52) U.S. Cl.
CPC ...... *A61F 13/2011* (2013.01); *A61F 13/2051* (2013.01); *A61F 13/34* (2013.01); *A61F 2013/1513* (2013.01)

(58) Field of Classification Search
CPC .. A61F 5/451; A61F 13/2011; A61F 13/2022; A61F 13/2042; A61F 13/2051; A61F 13/2057; A61F 13/34; A61F 2013/1513; A61F 2013/15138
See application file for complete search history.

(56) References Cited

U.S. PATENT DOCUMENTS

| | | | |
|---|---|---|---|
| 2,742,042 A | 4/1956 | Flanders | |
| 4,182,335 A | 1/1980 | Matrullo | |
| 4,484,919 A * | 11/1984 | Sohn | A61F 13/5611 604/358 |
| 4,880,417 A | 11/1989 | Yabrov | |
| 5,665,081 A | 9/1997 | Grosse | |
| D394,503 S | 5/1998 | Perrini | |
| 6,313,371 B1 | 11/2001 | Conant | |
| 8,062,277 B2 | 11/2011 | Fleming | |
| 2007/0093738 A1* | 4/2007 | Krecker | A61F 13/14 602/61 |
| 2015/0335495 A1* | 11/2015 | Wigder | A61F 13/28 604/385.01 |
| 2022/0008257 A1* | 1/2022 | Ladomi | A61F 13/2022 |

FOREIGN PATENT DOCUMENTS

CA 2341070 9/2002

* cited by examiner

*Primary Examiner* — Catharine L Anderson
*Assistant Examiner* — Lynne Anderson

(57) ABSTRACT

An absorptive anal hygiene apparatus for anal hygiene includes a sponge body having a body top side, a body bottom side, a body front side, a body back side, a body left side, and a body right side. The body bottom side is larger than the body top side. The sponge body is an absorptive material configured to be inserted within a user's buttocks adjacent the anus to prevent transfer of fecal matter from the user's anus to a user's clothing. A tab is coupled to the body top side of the sponge body. An extraction string is coupled to the tab. The extraction string is pullable to remove the sponge body from the user's buttocks.

9 Claims, 3 Drawing Sheets

ABSORPTIVE ANAL HYGIENE APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to anal hygiene device and more particularly pertains to a new anal hygiene device for anal hygiene.

(2) Description of Related Art Including Information Disclosed Under 37 CFR 1.97 and 1.98

The prior art relates to anal hygiene devices. Known devices are shaped and function similar to a feminine pad or a diaper. Such devices lack a shape that can be held within the user's buttocks adjacent the anus. These devices also lack an extraction string for easy, hygienic removal of the device after use.

BRIEF SUMMARY OF THE INVENTION

An embodiment of the disclosure meets the needs presented above by generally comprising a sponge body having a body top side, a body bottom side, a body front side, a body back side, a body left side, and a body right side. The body bottom side is larger than the body top side. The sponge body is an absorptive material configured to be inserted within a user's buttocks adjacent the anus to prevent transfer of fecal matter from the user's anus to a user's clothing. A tab is coupled to the body top side of the sponge body. An extraction string is coupled to the tab. The extraction string is pullable to remove the sponge body from the user's buttocks.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
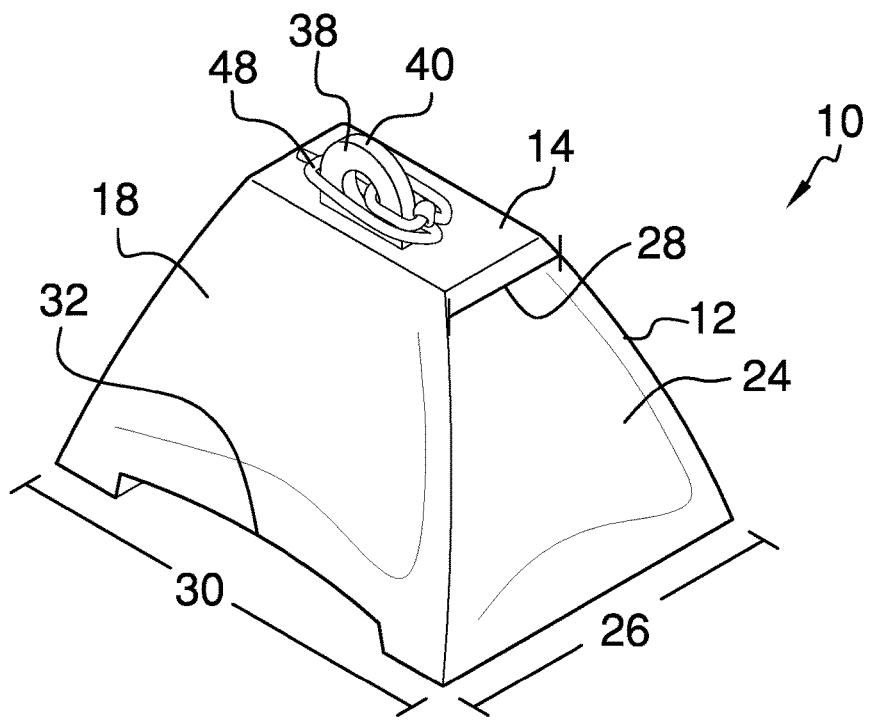
FIG. 1 is an isometric view of an absorptive anal hygiene apparatus according to an embodiment of the disclosure.
Figure 2:
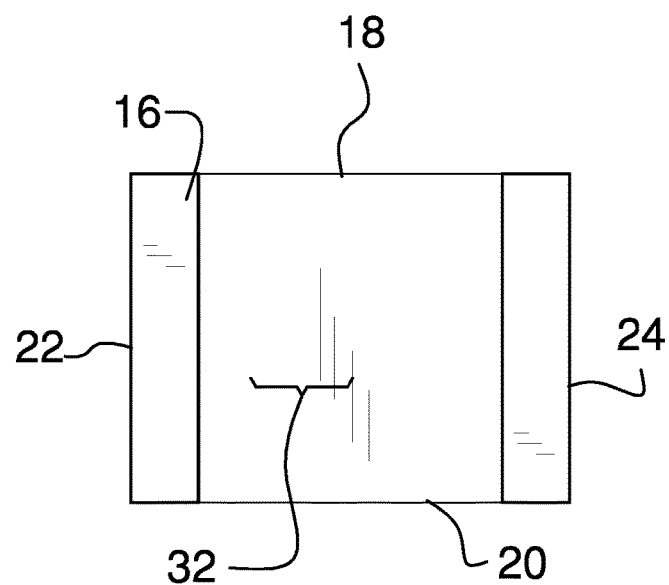
FIG. 2 is a bottom plan view of an embodiment of the disclosure.
Figure 3:
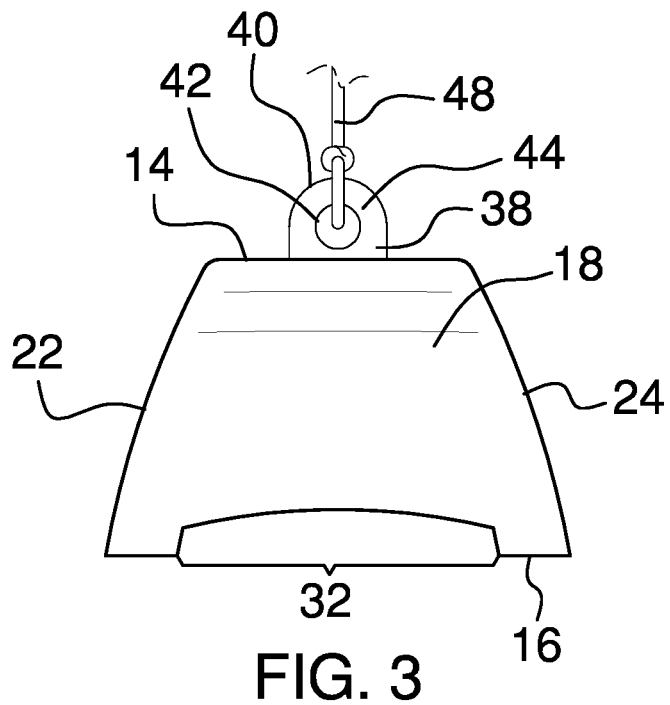
FIG. 3 is a front elevation view of an embodiment of the disclosure.
Figure 4:
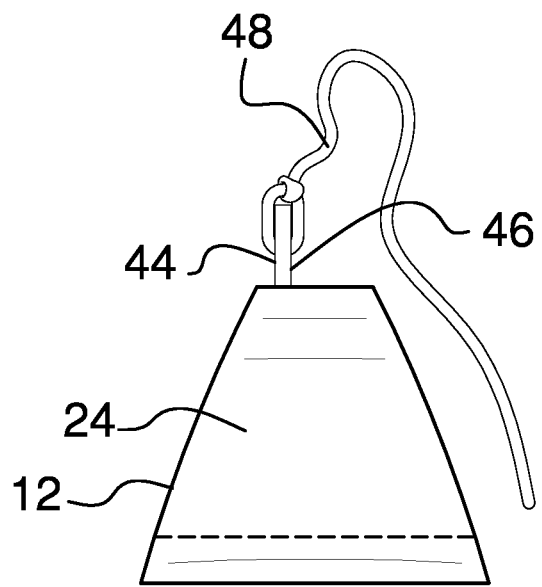
FIG. 4 is a side elevation view of an embodiment of the disclosure.
Figure 5:
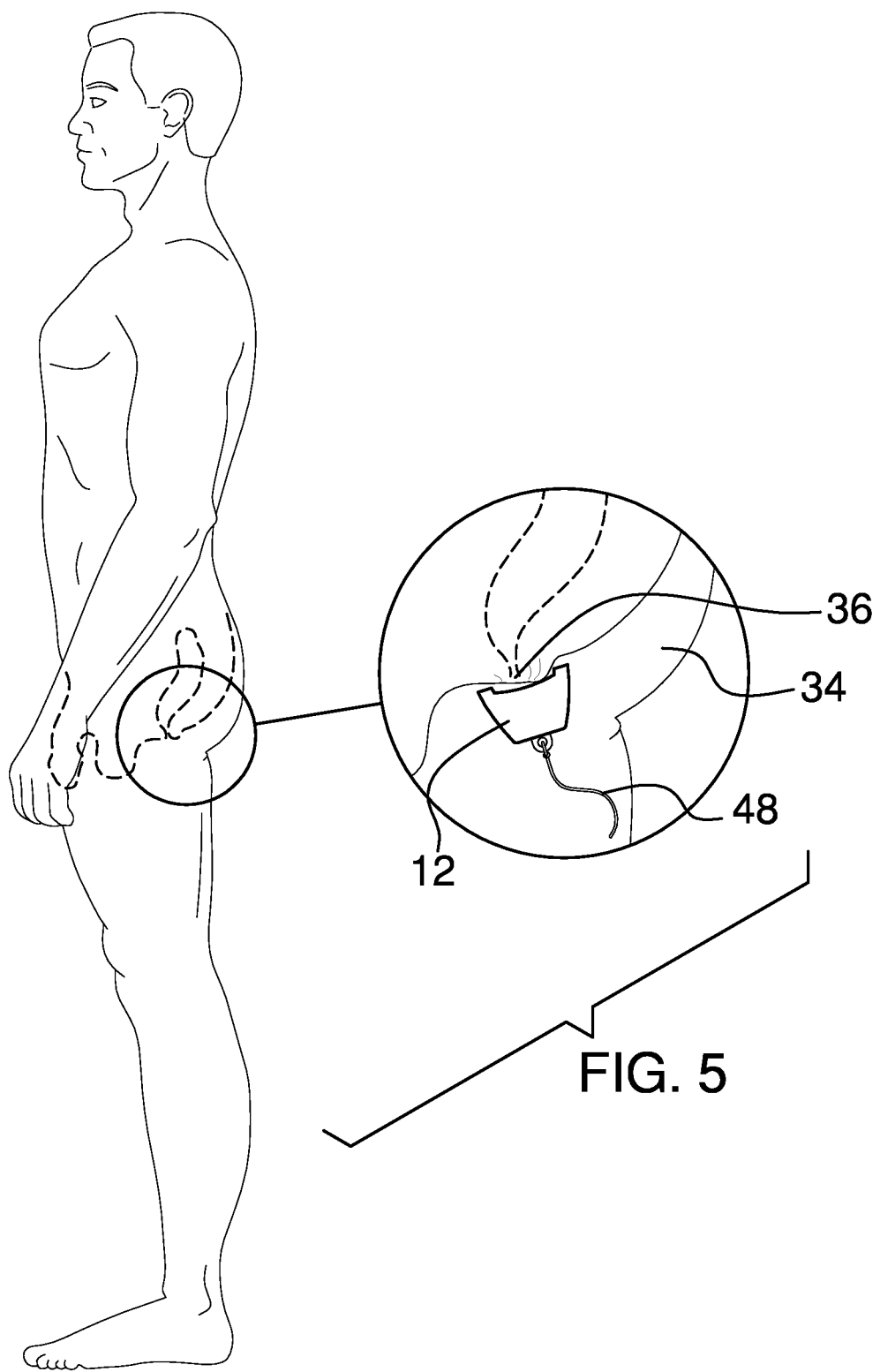
FIG. 5 is an in-use view of an embodiment of the disclosure.

With reference now to the drawings, and in particular to FIGS. 1 through 5 thereof, a new anal hygiene device embodying the principles and concepts of an embodiment of the disclosure and generally designated by the reference numeral 10 will be described.

As best illustrated in FIGS. 1 through 5, the absorptive anal hygiene apparatus 10 generally comprises a sponge body 12 having a body top side 14, a body bottom side 16, a body front side 18, a body back side 20, a body left side 22, and a body right side 24. Each of the body top side 14 and the body bottom side 16 have a rectangular profile.

The body bottom side 16 may be larger than the body top side 14. The body bottom side 16 may have a bottom width 26 equal to three times a top width 28 of the body top side. The body bottom side 16 may have a bottom length 30 equal to four times the top width 28. The bottom width 26, the top width 28, and the bottom length 30 may be 1½ inch, ½ inch, and 2 inches, respectively.

The body bottom side 16 may have a medial recessed portion 32. The recessed portion 32 may be arcuate for optimal absorption and capture. The sponge body 12 is an absorptive material configured to be inserted within a user's buttocks 34 adjacent the anus 36 to prevent transfer of fecal matter from the user's anus 36 to a user's clothing. The medial recessed portion 32 may occupy at least 75% of the bottom length 30.

A tab 38 is coupled to the sponge body 12. The tab 38 is coupled to the body top side 14 and may be offset more proximal the body front side 18. The tab 38 has a semicircular top edge 40 for user comfort and an attachment aperture 42 extending from a tab front side 44 through a tab back side 46.

An extraction string 48 is coupled to the tab 38. The extraction string 48 is coupled through the attachment aperture 42 for optimal security. The extraction string 48 is pullable to remove the sponge body 12 from the user's buttocks in the most hygienic way possible.

In use, the sponge body 12 is inserted within the user's buttock 34 such that the body bottom side 16 faces the user's anus 36. The sponge body 12 is never to be inserted within the anus 36. When done, the extraction string 48 is used to remove the sponge body 12.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An absorptive anal hygiene apparatus comprising:
   a sponge body having a body top side, a body bottom side, a body front side, a body back side, a body left side, and a body right side, the body bottom side being larger than the body top side, the sponge body being an absorptive material configured to be inserted within a user's buttocks adjacent the anus to prevent transfer of fecal matter from the user's anus to a user's clothing;
   a tab coupled to the sponge body, the tab being coupled to the body top side; and
   an extraction string coupled to the tab, the extraction string being pullable to remove the sponge body from the user's buttocks.

2. The absorptive anal hygiene apparatus of claim 1 further comprising each of the body top side and the body bottom side having a rectangular profile.

3. The absorptive anal hygiene apparatus of claim 1 further comprising the body bottom side having a medial recessed portion.

4. The absorptive anal hygiene apparatus of claim 1 further comprising the body bottom side having a bottom width equal to three times a top width of the body top side.

5. The absorptive anal hygiene apparatus of claim 4 further comprising the body bottom side having a bottom length equal to four times the top width.

6. The absorptive anal hygiene apparatus of claim 1 further comprising the tab having a semicircular top edge and an attachment aperture extending from a tab front side through a tab back side; the extraction string being coupled through the attachment aperture.

7. The absorptive anal hygiene apparatus of claim 3 further comprising the medial recessed portion being arcuate.

8. The absorptive anal hygiene apparatus of claim 1 further comprising the tab being coupled to the body top side proximal the body front side.

9. An absorptive anal hygiene apparatus comprising:
   a sponge body having a body top side, a body bottom side, a body front side, a body back side, a body left side, and a body right side, each of the body top side and the body bottom side having a rectangular profile, the body bottom side being larger than the body top side, the body bottom side having a bottom width equal to three times a top width of the body top side, the body bottom side having a bottom length equal to four times the top width, the body bottom side having a medial recessed portion, the recessed portion being arcuate, the sponge body being an absorptive material configured to be inserted within a user's buttocks adjacent the anus to prevent transfer of fecal matter from the user's anus to a user's clothing;
   a tab coupled to the sponge body, the tab being coupled to the body top side proximal the body front side, the tab having a semicircular top edge and an attachment aperture extending from a tab front side through a tab back side; and
   an extraction string coupled to the tab, the extraction string being coupled through the attachment aperture, the extraction string being pullable to remove the sponge body from the user's buttocks.

* * * * *